(12) United States Patent
Schneider et al.

(10) Patent No.: US 6,911,547 B1
(45) Date of Patent: Jun. 28, 2005

(54) PROCESS FOR THE PREPARATION OF BICYCLIC DIKETONE SALTS

(75) Inventors: Hermann Schneider, Basel (CH); Christoph Lüthy, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 204 days.

(21) Appl. No.: 10/408,950

(22) Filed: Apr. 8, 2003

(30) Foreign Application Priority Data

Apr. 9, 2002 (CH) ................................................ 597/02

(51) Int. Cl.[7] ........................ C07D 313/02; C07C 45/27
(52) U.S. Cl. ...................................... 549/266; 568/315
(58) Field of Search ............................ 549/266; 568/315

(56) References Cited

U.S. PATENT DOCUMENTS 3,932,510 A    1/1976   Muller

FOREIGN PATENT DOCUMENTS

| CH | 680044 | 6/1992 |
|---|---|---|
| JP | 10265441 A | 10/1998 |
| WO | 00/15615 | 3/2000 |
| WO | 00/37437 | 6/2000 |
| WO | 01/66522 | 9/2001 |
| WO | 01/94339 | 12/2001 |

OTHER PUBLICATIONS

Qudrat–I–Khuda M., "XXIX. Studies in Keto–Iactol Tautomerism. Part IV, Chemistry of 5–acetyl–1:1:2–trimethylcyclopentane–2–carboxylic Acid. Observations on the Constitutions of the Acid Esters of Camphoric Acid and a Synthesis of Homoepicamphor", Journal of the Chemical Society, 1920, pp. 206–213.

*Primary Examiner*—Taofiq Solola
(74) *Attorney, Agent, or Firm*—Thomas Hamilton

(57) ABSTRACT

The present invention relates to a process for the preparation of bicyclic 1,3-diketone salts of formula I

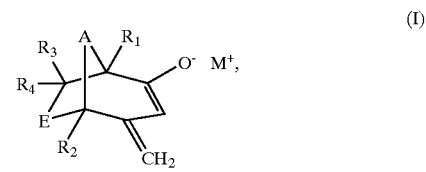

wherein $R_1$, $R_2$, $R_3$ and $R_4$ are each independently of the others hydrogen or $C_1$–$C_4$alkyl; A and E are each independently of the other $C_1$–$C_2$alkylene, which may be substituted once or up to four times by a $C_1$–$C_4$alkyl group, and $M^+$ is an alkali metal ion, alkaline earth metal ion or ammonium ion, by oxidation of a compound of formula II

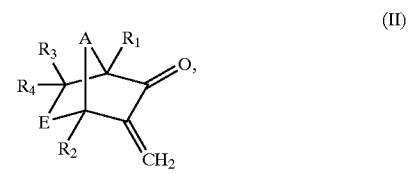

to a compound of formula III

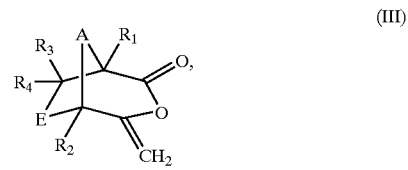

and subsequent conversion to a compound of formula I either in the presence of a base and a catalytic amount of a cyanide or in the presence of an alkali metal alcoholate or alkaline earth metal alcoholate, and to novel bicyclic enol lactone intermediates of formula III for use in that process.

2 Claims, No Drawings

PROCESS FOR THE PREPARATION OF BICYCLIC DIKETONE SALTS

The present invention relates to a process for the preparation of bicyclic 1,3-diketone salts and to novel bicyclic enol lactone intermediates for use in that process.

Bicyclic 1,3-diketones, such as, for example, bicyclo[3.2.1]octane-2,4-dione, are valuable intermediates in the preparation of herbicides, such as are described, for example, in WO 00/15615, WO 00/37437, WO 01/66522 and WO 01/94339.

A number of processes are known for the preparation of such 1,3-diketones. For example, the bicyclic 1,3-diketones can be obtained from the corresponding salt forms according to known methods.

Such a process for the preparation of bicyclic 1,3-diketones from the corresponding salts is described, for example, in JP-10-265441. The use of 3-acetyl-cyclopentanecarboxylic acid alkyl esters, which are obtained from 3-methylene-bicyclo[2.2.1]heptan-2-one, as starting materials for the commercial preparation of bicyclo[3.2.1]octane-2,4-dione via the corresponding sodium salt renders that process too uneconomical, since the oxidative ring-opening in the presence of acids and alcohols, for example using sulfurous peroxo acid in the presence of methanol, can result not only in the desired alkyl esters but also in the formation of the free 3-acetylcyclopentanecarboxylic acid, which needs to be converted back to the corresponding alkyl ester, in an additional reaction step, prior to cyclisation.

The aim of the present invention is therefore to provide a novel process for the preparation of bicyclic 1,3-diketone salts that enables those salts to be prepared economically in high yields and with good quality.

The present invention accordingly relates to a process for the preparation of compounds of formula I

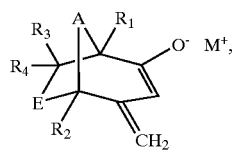

wherein $R_1$, $R_2$, $R_3$ and $R_4$ are each independently of the others hydrogen, $C_1$–$C_4$alkyl, halogen, hydroxy, $C_1$–$C_4$alkoxy, $C_1$–$C_4$alkoxycarbonyl, hydroxycarbonyl or cyano; A and E are each independently of the other $C_1$–$C_2$alkylene, which may be substituted once or up to four times by a $C_1$–$C_4$alkyl group or by halogen, hydroxy, $C_1$–$C_4$alkoxy, $C_1$–$C_4$alkoxy-carbonyl or cyano, and M+ is an alkali metal ion, alkaline earth metal ion or ammonium ion, which process comprises a) reacting a compound of formula II

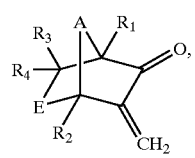

wherein $R_1$, $R_2$, $R_3$, $R_4$, A and E are as defined for formula I, in the presence of an oxidising agent, to form a compound of formula III

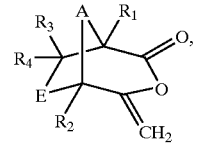

wherein $R_1$, $R_2$, $R_3$, $R_4$, A and E are as defined for formula I, and b) then converting that compound to a salt of formula I either in the presence of a base and a catalytic amount of a cyanide or in the presence of an alkali metal alcoholate or alkaline earth metal alcoholate or a hydroxide.

The alkyl groups in the above substituent definitions may be straight-chain or branched and are, for example, methyl, ethyl, n-propyl, isopropyl, n-butyl, sec-butyl, isobutyl or tert-butyl. Alkoxy is, for example, methoxy, ethoxy, propoxy, isopropoxy, n-butoxy, isobutoxy, sec-butoxy or tert-butoxy. Alkoxycarbonyl is, for example, methoxycarbonyl, ethoxycarbonyl, propoxycarbonyl, isopropoxycarbonyl, n-butoxycarbonyl, isobutoxycarbonyl, sec-butoxy-carbonyl or tert-butoxycarbonyl; preferably methoxycarbonyl or ethoxycarbonyl.

M+ as an alkali metal ion, alkaline earth metal ion or ammonium ion is, for example, the sodium, potassium, calcium, magnesium, triethylammonium or diisopropylethylammonium cation.

For a better illustration of the linking sites of the bicyclic compound, the compounds of formula I may also be depicted as follows

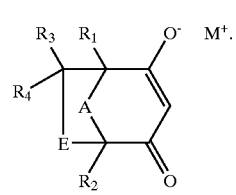

Since, in compounds of formula III, which may be prepared from chiral compounds of formula II, chiral forms may also occur, such as, for example, in

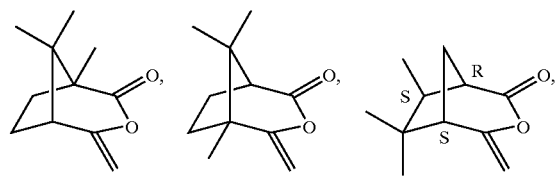

the present invention also includes all such chiral forms, processes for the preparation thereof and the use thereof in the preparation of chiral compounds of formula I.

Salts of formula I may also occur in tautomeric forms, as illustrated:

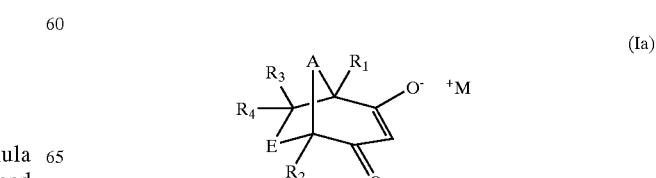

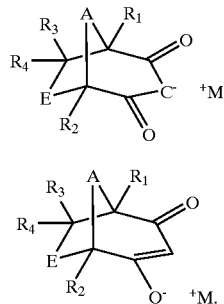

(Ib)

(Ic)

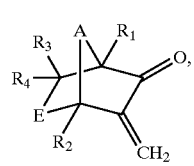

The compounds of formula II are known or are obtainable according to known methods. The preparation of a compound of formula II wherein $R_1$, $R_2$, $R_3$ and $R_4$ are hydrogen, A is methylene and E is methylene is described, for example, in JP-10-265415.

The process according to the invention is suitable especially for the preparation of compounds of formula I wherein
a) $R_1$, $R_2$, $R_3$ and $R_4$ are each independently of the others hydrogen or $C_1$–$C_4$alkyl, A and E are each independently of the other $C_1$–$C_2$alkylene which may be substituted once or up to four times by a $C_1$–$C_4$alkyl group, and M+ is an alkali metal ion, alkaline earth metal ion or ammonium ion;
b) $R_1$ and $R_2$ are each independently of the other hydrogen or methyl;
c) $R_3$ and $R_4$ are each independently of the other hydrogen or methyl;
d) A is methylene which may be substituted once or twice by a methyl group, or ethylene;
e) E is methylene which may be substituted once or twice by a methyl group; and/or
f) M+ is the sodium, triethylammonium or diisopropylethylammonium cation.

The process according to the invention is suitable more especially for the preparation of compounds of formula I wherein $R_1$, $R_2$, $R_3$ and $R_4$ are hydrogen, A is methylene, E is methylene and M+ is the sodium, triethylammonium or diisopropylethylammonium cation.

Reaction Step a):

Ketones can be oxidised to alkyl esters in the presence of oxidising agents, such as peracids, for example peracetic acid, m-chloroperbenzoic acid or trifluoroperacetic acid, hydrogen peroxide or hydrogen peroxide in the presence of catalytic amounts of selenium dioxide, a carbon atom migrating to the newly inserted oxygen grouping. Such a reaction is generally known as a Baeyer-Villiger rearrangement. It is also known, from specialist chemical literature, that various steric, conformational and electronic effects and effects caused by ring strain determine the position in which the oxygen is inserted vicinally to the carbonyl group. Consequently, it is to be regarded as surprising that, in the strained-ring bicyclic exomethylene ketones of formula II according to the invention

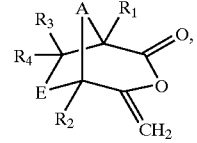

(II)

wherein $R_1$, $R_2$, $R_3$, $R_4$, A and E are as defined for formula I, it is possible for the oxygen grouping to be positioned with a high level of selectivity between the carbonyl group and the exomethylene group and that thereby bicyclic enol lactones of formula III (III)

that are isolatable, stable and—of great advantage for an industrial process—distillable, can be obtained.

For some compounds of formula III, for example for bicyclo[3.2.1]octane-2,4-dione, the process has special economic and ecological advantages, since the starting materials used are petrochemical raw materials which, by means of addition reactions, condensation reactions with the removal of water and, in principle, using hydrogen peroxide as oxidising agent, efficiently lead to the product of formula III without generating harmful effluents.

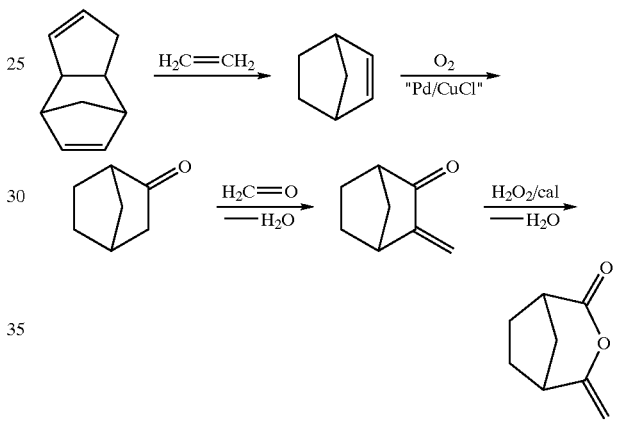

In reaction step a), preferred oxidising agents for the conversion of compounds of formula II to compounds of formula III are organic peracids, such as peracetic acid, trifluoroperacetic acid, performic acid, perpropionic acid, perbenzoic acid, m-chloroperbenzoic acid or monoperoxyphthalic acid, hydrogen peroxide or hydrogen peroxide in the presence of catalytic amounds of selenium dioxide, where appropriate in the presence of an additional amount of base.

The reaction according to reaction step a) is preferably carried out in the presence of a base in an inert solvent at temperatures of from −20° C. to 50° C., especially from −15° C. to +15° C. Suitable solvents include, for example, dichloromethane, dichloroethane, acetic acid, acetic anhydride and mixtures thereof, e.g. dichloromethane and acetic acid or acetic acid and acetic anhydride. Suitable bases include, for example, sodium acetate, potassium acetate, sodium carbonate, sodium hydrogen carbonate, potassium carbonate, calcium carbonate, barium oxide, potassium hydrogen phosphate and potassium dihydrogen phosphate, especially sodium acetate trihydrate when hydrogen peroxide in acetic acid is used. The base is used in an amount of from 0.1 up to about 6 equivalents, preferably from 1 to 3 equivalents. When a catalytic amount of selenium dioxide is used, preferably the selenium dioxide is used only in very small amounts of approximately from 0.0001 to 1%.

The oxidising agent in reaction step a) can be used in less than stoichiometric amount, or in equimolar amounts or up to a slight excess of up to 1.4 equivalents. The oxidising agent is preferably used in less than stoichiometric amount. In order to avoid loss of selectivity as a result of further oxidation of the compound of formula III, oxidation up to a conversion of from 40% to 85%, especially from 50% to 70%. Is preferred, unreacted starting material being recycled. After destroying excess oxidising agent and extractive working up according to customary methods, the starting material of formula II can advantageously be recovered in the form of a lower-boiling distillate. Such a procedure is advantageous especially for the industrial-scale preparation of compounds of formula I and their further use in the preparation of bicyclic 1,3-diketones, since the products obtained have a high level of purity, are very largely free of residues and, because they are in liquid form, have good transport properties (for example can be transported through pipes). The distillation residue can either be used directly for the preparation of the salts of formula I or. If required, concentrated by distillation to a content of from 90 to 99%, for example for the preparation of pure bicyclic 1,3-diketone derivatives from direct reaction with salts of formula I.

Process Step b):

It is known that some 6-methylenetetrahydropyran-2-ones can be converted directly to 1,3-cyclohexanediones in the presence of bases, such as, for example, sodium methanolate, by heating in anhydrous benzene. Such a process is described in J. Gen. Chem. USSR, 1964, 34, 3509 for the preparation of 4,4-dimethylcyclohexane-1,3-dione and 4-phenylcyclo-hexane-1,3-dione.

It has now been discovered that that process can very advantageously be applied to the conversion of the enol lactones of formula III to the strained-ring bicyclic 1,3-diketone salts of formula I according to process step b).

For that purpose, a compound of formula III is reacted in the presence of at least catalytic amounts of alkali metal alcoholate and alkaline earth metal alcoholate ions in a solvent. The alkali metal and alkaline earth metal alcoholates can be used in catalytic or stoichiometric amounts in that reaction. When catalytic amounts are used it is necessary to add a further base. The further base may be added in stoichiometric amounts or in excess. It is more advantageously used in stoichiometric amount up to a slight excess. As additional bases there may used, for example. Inorganic bases, such as carbonates, for example potassium carbonate, hydroxides, for example sodium hydroxide and potassium hydroxide, oxides, for example barium oxide, and hydrides, for example sodium hydride. Catalytic amounts of alkali metal and alkaline earth metal alcoholates are to be understood as being from 0.0001% to 25%, preferably from 1% to 10%.

In a preferred embodiment of the process according to the invention, the alcoholates of alkali metals and alkaline earth metals, especially those of lithium, sodium and potassium, are used without an additional base, in stoichiometric amounts or in excess, but especially preferably in stoichiometric amounts.

Preferred alkali metal and alkaline earth metal alcoholates are those of lithium, sodium and potassium, especially the methanolates and ethanolates. Alkali metal and alkaline earth metal alcoholates that are especially preferred are sodium methanolate, sodium ethanolate, sodium isopropanolate, sodium n-butanolate, potassium tert-butanolate, sodium pentanolate, sodium tert-pentanolate, sodium amylate and sodium 2-methoxyethanolate; sodium methanolate is more especially preferred. The use of anhydrous hydroxides, for example lithium hydroxide, sodium hydroxide or potassium hydroxide, is likewise suitable.

Solvents suitable for the conversion are toluene, xylene, chlorobenzene, methylnaphthalene, or alcohols such as methanol, ethanol, isopropanol, amyl alcohol, or tetrahydrofuran or dioxane, or aprotic solvents such as propionitrile, dimethylformamide, N-methylpyrrolidone or dimethyl sulfoxide, or 2-methyl-5-ethylpyridine or the like, or mixtures of such solvents, for example toluene and dimethylformamide or toluene and N-methylpyrrolidone.

In reaction step b), special preference is given to the use of toluene and, as additional solvent, dimethylformamide or N-methylpyrrolidone, since then the compounds of formula I can especially advantageously be precipitated from the reaction mixture and consequently further base-catalysed secondary reactions are substantially avoided.

In reaction step b), the solvent or the solvents is/are used in an amount at which the salt, preferably the sodium salt, is precipitated in readily crystallisable form from the reaction medium and the reaction mixture nevertheless remains readily stirrable. In the conversion of compounds of formula III to compounds of formula I wherein M+ is an alkali metal cation, preferably the sodium cation, especially solvent mixtures of toluene and approximately from 1 to 15% dimethylformamide or approximately from 1 to 15% N-methylpyrrolidone are advantageous, special preference being given to a mixture of approximately from 3 to 8% dimethylformamide in toluene.

Depending on the solvent, the conversions are carried out at temperatures of approximately from 0° C. to the boiling temperature and more advantageously under anhydrous conditions. In an especially advantageous variant, the conversion is carried out in toluene using sodium methanolate in methanol as the base at a temperature of from 80° C. up to the boiling temperature, during which the methanol released is continuously distilled off in order to avoid secondary reactions.

Especially, sodium methanolate in the form of an approximately 30% methanolic solution in a mixture of toluene and approximately from 1 to 15% dimethylformamide can be used as initial charge, with the result that, on heating, first of all the methanol is distilled off up to a column head temperature of approximately from 105 to 110° C., and only then is the compound of formula III, dissolved in a small amount of toluene, added dropwise in such a manner that the methanol released is continuously removed from the reaction mixture by further distillation and hence the salt of formula I is able to precipitate from the reaction mixture in the form of a pure, readily stirrable crystallisate.

It is advantageous that, when the conversion is carried out using alcoholate anions as catalyst, also the corresponding alcoholate-forming cation is used as the base for the precipitation of the enolate of formula I. Suitable amounts of alkali metal alcoholate are from 1.0 up to 2.5 equivalents, especially from 1.0 up to approximately 1.5 equivalents. Special preference is given to from 1.0001 to 1.1 equivalents of sodium methanolate as the base.

The compounds of formula I can either be used-directly in the reaction mixture for further conversions or alternatively isolated. The compounds of formula I can be isolated from the reaction mixture by filtration in accordance with customary methods. Another possibility is the further conversion of the compounds of formula I to the corresponding neutral bicyclic 1,3-diketones which, as already mentioned above, serve as intermediates in the production of herbicides.

For that purpose, when sodium methanolate in a mixture of toluene and a small amount of dimethylformamide or N-methylpyrrolidone is used, either the compounds of formula I, especially sodium salts thereof, can be filtered off, then neutralised in aqueous solution using acid, e.g. hydrochloric acid, sulfuric acid or acetic acid, and subsequently isolated by means of an extracting agent, for example ethyl acetate, tert-butyl methyl ether, dichloro-methane, dichloroethane or chlorobenzene, or the sodium-salt-containing reaction mixture can be neutralised directly, by introducing, with stirring, an aqueous acid, e.g. a 2N to 10N hydrochloric acid, and then extracted, where appropriate by adding a further diluent, for example ethyl acetate. In order to obtain the neutral bicyclic 1,3-diketones. The neutralisation is advantageously carried out with pH control, and the 1,3-diketones obtained are extracted in a pH range of approximately from 2 to 7, especially approximately from 4 to 6.

In another embodiment of the process according to the invention. In reaction step b) catalytic amounts of cyanide ions are used in the presence of an additional base. Suitable bases are especially tertiary amines, such as trialkylamines, e.g. trimethylamine, triethylamine, diisopropylethylamine (Hünig's base), tri-n-butylamine, N,N-dimethylaniline and N-methyl-morpholine. Bases such as anhydrous sodium hydroxide, sodium hydrogen carbonate and potassium carbonate are also suitable. As a source of cyanide ions there are preferably used the alkali metal cyanides, e.g. sodium cyanide or potassium cyanide, or copper(I) cyanide, or organic cyanohydrins, such as acetone cyanohydrin, or trialkylsilyl cyanides, such as trimethylsilyl cyanide, or tertiary ammonium bases, such as tetraethylammonium cyanide. In that process variant according to the invention, the amount of alkali metal cyanide used ranges from a small amount up to a slight excess. The cyanides are used in amounts of from 0.1% up to approximately 25%, preferably from 1% to approximately 15%, in the presence of an additional base, such as especially triethylamine or Hünig's base, the amount of base being from 1 to 6 equivalents, especially from 1.1 to approximately 2.5 equivalents.

That embodiment of the process according to the invention is preferably carried out in an inert solvent; such as n-heptane, toluene, xylene, dichloromethane, dichloroethane, dimethoxyethane, tetrahydrofuran, dioxane, tert-butyl methyl ether, ethyl acetate, acetone, 2-butanone, acetonitrile, propionitrile, dimethylformamide or N-methylpyrroildone, at temperatures of from −5° C. to approximately +80° C., especially preferably in acetonitrile or dichloromethane at temperatures of from approximately 10° C. to approximately 60° C.

There may optionally be used for the conversions in reaction step b), depending on the solvents employed, additives such as, for example, lithium chloride or lithium bromide, or phase transfer catalysts, such as, for example, tetrabutylammonium bromide or especially tetraethylammonium cyanide, or drying agents, such as magnesium sulfate or suitable molecular sieves, but such additives are generally not required.

It is also possible in that embodiment of the process for the preparation of compounds of formula I for the latter either to be isolated or to be used directly in the reaction mixture for further reactions, for example to form herbicidally active compounds, as mentioned above. The ammonium salts of formula I so obtained can be isolated, for example, after filtering off small amounts of solids, such as the potassium salt of formula I when potassium cyanide is used as the catalyst, by simple concentration of the reaction mixture by evaporation.

It is also possible for the compounds of formula I to be further reacted to form the corresponding neutral bicyclic 1,3-diketones which, as mentioned above, serve as intermediates in the production of herbicides. For that purpose it is possible to free the neutral bicyclic 1,3-diketones by adding water and an acid as neutralising agent, for example hydrochloric acid or sulfuric acid, and then, with control of the pH in a range of approximately from 2 to 7, especially approximately from 4 to 6, to isolate them by means of an extracting agent, for example ethyl acetate, tert-butyl methyl ether, dichloromethane, dichloroethane or chlorobenzene.

The compounds of formula III

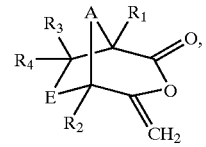

(III)

wherein $R_1$, $R_2$, $R_3$, $R_4$, A and E are as defined for formula I, are valuable intermediates in the preparation of compounds of formula I and have been developed especially for the present process according to the invention. The present invention accordingly relates also to, those compounds.

Compounds of formula III especially valuable for the preparation of compounds of formula I are especially those wherein a) $R_1$ and $R_2$ are each independently of the other hydrogen or methyl;

b) $R_3$ and $R_4$ are each independently of the other hydrogen or methyl;

c) A is methylene which may be substituted once or twice by a methyl group, or ethylene; and/or d) E is methylene which may be substituted once or twice by a methyl group.

As an intermediate in the preparation of compounds of formula I there is especially suitable a compound of formula III wherein $R_1$, $R_2$, $R_3$ and $R_4$ are hydrogen, A is methylene and E is methylene. Preferred compounds of formula III are listed in the following Table:

TABLE 1

Compounds of formula III:

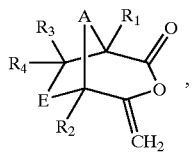

(III)

| Comp. No. | $R_1$ | $R_2$ | $R_3$ | $R_4$ | A | E |
|---|---|---|---|---|---|---|
| 1.001 | H | H | H | H | $CH_2$ | $CH_2$ |
| 1.002 | $CH_3$ | H | H | H | $CH_2$ | $CH_2$ |
| 1.003 | $C_2H_5$ | H | H | H | $CH_2$ | $CH_2$ |
| 1.004 | n-$C_3H_7$ | H | H | H | $CH_2$ | $CH_2$ |
| 1.005 | iso-$C_3H_7$ | H | H | H | $CH_2$ | $CH_2$ |
| 1.006 | n-$C_4H_9$ | H | H | H | $CH_2$ | $CH_2$ |

TABLE 1-continued

Compounds of formula III:

(III)

| Comp. No. | R₁ | R₂ | R₃ | R₄ | A | E |
|---|---|---|---|---|---|---|
| 1.007 | iso-C₄H₉ | H | H | H | CH₂ | CH₂ |
| 1.008 | sec-C₄H₉ | H | H | H | CH₂ | CH₂ |
| 1.009 | tert-C₄H₉ | H | H | H | CH₂ | CH₂ |
| 1.010 | H | CH₃ | H | H | CH₂ | CH₂ |
| 1.011 | CH₃ | CH₃ | H | H | CH₂ | CH₂ |
| 1.012 | C₂H₅ | CH₃ | H | H | CH₂ | CH₂ |
| 1.013 | n-C₃H₇ | CH₃ | H | H | CH₂ | CH₂ |
| 1.014 | iso-C₃H₇ | CH₃ | H | H | CH₂ | CH₂ |
| 1.015 | n-C₄H₉ | CH₃ | H | H | CH₂ | CH₂ |
| 1.016 | iso-C₄H₉ | CH₃ | H | H | CH₂ | CH₂ |
| 1.017 | sec-C₄H₉ | CH₃ | H | H | CH₂ | CH₂ |
| 1.018 | tert-C₄H₉ | CH₃ | H | H | CH₂ | CH₂ |
| 1.019 | H | CH₃ | CH₃ | H | CH₂ | CH₂ |
| 1.020 | CH₃ | CH₃ | CH₃ | H | CH₂ | CH₂ |
| 1.021 | C₂H₅ | CH₃ | CH₃ | H | CH₂ | CH₂ |
| 1.022 | n-C₃H₇ | CH₃ | CH₃ | H | CH₂ | CH₂ |
| 1.023 | iso-C₃H₇ | CH₃ | CH₃ | H | CH₂ | CH₂ |
| 1.024 | n-C₄H₉ | CH₃ | CH₃ | H | CH₂ | CH₂ |
| 1.025 | iso-C₄H₉ | CH₃ | CH₃ | H | CH₂ | CH₂ |
| 1.026 | sec-C₄H₉ | CH₃ | CH₃ | H | CH₂ | CH₂ |
| 1.027 | tert-C₄H₉ | CH₃ | CH₃ | H | CH₂ | CH₂ |
| 1.028 | H | CH₃ | CH₃ | CH₃ | CH₂ | CH₂ |
| 1.029 | CH₃ | CH₃ | CH₃ | CH₃ | CH₂ | CH₂ |
| 1.030 | C₂H₅ | CH₃ | CH₃ | CH₃ | CH₂ | CH₂ |
| 1.031 | n-C₃H₇ | CH₃ | CH₃ | CH₃ | CH₂ | CH₂ |
| 1.032 | iso-C₃H₇ | CH₃ | CH₃ | CH₃ | CH₂ | CH₂ |
| 1.033 | n-C₄H₉ | CH₃ | CH₃ | CH₃ | CH₂ | CH₂ |
| 1.034 | iso-C₄H₉ | CH₃ | CH₃ | CH₃ | CH₂ | CH₂ |
| 1.035 | sec-C₄H₉ | CH₃ | CH₃ | CH₃ | CH₂ | CH₂ |
| 1.036 | tert-C₄H₉ | CH₃ | CH₃ | CH₃ | CH₂ | CH₂ |
| 1.037 | H | CH₃ | CH₃ | CH₃ | CH₂CH₂ | CH₂ |
| 1.038 | CH₃ | CH₃ | CH₃ | CH₃ | CH₂CH₂ | CH₂ |
| 1.039 | C₂H₅ | CH₃ | CH₃ | CH₃ | CH₂CH₂ | CH₂ |
| 1.040 | n-C₃H₇ | CH₃ | CH₃ | CH₃ | CH₂CH₂ | CH₂ |
| 1.041 | iso-C₃H₇ | CH₃ | CH₃ | CH₃ | CH₂CH₂ | CH₂ |
| 1.042 | n-C₄H₉ | CH₃ | CH₃ | CH₃ | CH₂CH₂ | CH₂ |
| 1.043 | iso-C₄H₉ | CH₃ | CH₃ | CH₃ | CH₂CH₂ | CH₂ |
| 1.044 | sec-C₄H₉ | CH₃ | CH₃ | CH₃ | CH₂CH₂ | CH₂ |
| 1.045 | tert-C₄H₉ | CH₃ | CH₃ | CH₃ | CH₂CH₂ | CH₂ |
| 1.046 | H | CH₃ | CH₃ | CH₃ | CH₂CH₂ | CH₂CH₂ |
| 1.047 | CH₃ | CH₃ | CH₃ | CH₃ | CH₂CH₂ | CH₂CH₂ |
| 1.048 | C₂H₅ | CH₃ | CH₃ | CH₃ | CH₂CH₂ | CH₂CH₂ |
| 1.049 | n-C₃H₇ | CH₃ | CH₃ | CH₃ | CH₂CH₂ | CH₂CH₂ |
| 1.050 | iso-C₃H₇ | CH₃ | CH₃ | CH₃ | CH₂CH₂ | CH₂CH₂ |
| 1.051 | n-C₄H₉ | CH₃ | CH₃ | CH₃ | CH₂CH₂ | CH₂CH₂ |
| 1.052 | iso-C₄H₉ | CH₃ | CH₃ | CH₃ | CH₂CH₂ | CH₂CH₂ |
| 1.053 | sec-C₄H₉ | CH₃ | CH₃ | CH₃ | CH₂CH₂ | CH₂CH₂ |
| 1.054 | tert-C₄H₉ | CH₃ | CH₃ | CH₃ | CH₂CH₂ | CH₂CH₂ |
| 1.055 | H | CH₃ | CH₃ | CH₃ | CH₂ | CH₂CH₂ |
| 1.056 | CH₃ | CH₃ | CH₃ | CH₃ | CH₂ | CH₂CH₂ |
| 1.057 | C₂H₅ | CH₃ | CH₃ | CH₃ | CH₂ | CH₂CH₂ |
| 1.058 | n-C₃H₇ | CH₃ | CH₃ | CH₃ | CH₂ | CH₂CH₂ |
| 1.059 | iso-C₃H₇ | CH₃ | CH₃ | CH₃ | CH₂ | CH₂CH₂ |
| 1.060 | n-C₄H₉ | CH₃ | CH₃ | CH₃ | CH₂ | CH₂CH₂ |
| 1.061 | iso-C₄H₉ | CH₃ | CH₃ | CH₃ | CH₂ | CH₂CH₂ |
| 1.062 | sec-C₄H₉ | CH₃ | CH₃ | CH₃ | CH₂ | CH₂CH₂ |
| 1.063 | tert-C₄H₉ | CH₃ | CH₃ | CH₃ | CH₂ | CH₂CH₂ |
| 1.064 | H | H | H | H | CHCH₃ | CH₂ |
| 1.065 | CH₃ | H | H | H | CHCH₃ | CH₂ |
| 1.066 | CH₃ | H | H | H | C(CH₃)₂ | CH₂ |
| 1.067 | H | CH₃ | H | H | C(CH₃)₂ | CH₂ |
| 1.068 | H | H | H | H | C(CH₃)₂ | CH₂ |
| 1.069 | H | H | CH₃ | CH₃ | CH₂ | CH(CH₃) |
| 1.070 | H | H | H | H | CH₂CH₂ | CH₂ |
| 1.071 | H | H | CH₃ | H | CH₂CH₂ | CH₂ |
| 1.072 | H | H | H | H | CH₂ | CH(CH₃) |

TABLE 1-continued

Compounds of formula III:

(III)

[Structure showing bicyclic compound with R1, R2, R3, R4, A, E substituents and CH2 group]

| Comp. No. | R₁ | R₂ | R₃ | R₄ | A | E |
|---|---|---|---|---|---|---|
| 1.073 | H | H | H | H | $CH_2CH_2$ | $CH(CH_3)$ |
| 1.074 | H | $CH_2CH_3$ | H | H | $CH_2$ | $CH_2$ |
| 1.075 | $CH_3$ | H | H | H | $CH_2$ | $CH_2C(CH_3)_2$ |
| 1.076 | $CH_3$ | $CH(CH_3)_2$ | H | H | $CH_2CH_2$ | $CH_2$ |
| 1.077 | H | H | $CH_3$ | H | $CH_2$ | $C(CH_3)_2$ |
| 1.078 | Cl | H | H | H | $C(CH_3)_2$ | $CH_2$ |
| 1.079 | CN | H | H | H | $C(CH_3)_2$ | $CH_2$ |
| 1.080 | $COOCH_3$ | H | H | H | $CH_2$ | $CH_2$ |
| 1.081 | COOH | H | H | H | $CH_2$ | $CH_2$ |
| 1.082 | $OCH_3$ | H | H | H | $CH_2$ | $CH_2$ |
| 1.083 | $OCH_2CH_3$ | H | H | H | $CH_2$ | $CH_2$ |
| 1.084 | H | H | H | H | CH(Cl) | $CH_2CH_2$ |
| 1.085 | H | H | H | H | $CH_2$ | CH(Cl) |
| 1.086 | H | H | H | Br | $CH_2$ | $CH_2$ |
| 1.087 | H | $OCH_3$ | H | H | $CH_2CH_2$ | $CH(COO-CH_3)$ |
| 1.088 | $CH_3$ | $OCH_3$ | $CH_3$ | H | $CH_2CH_2$ | $CH(COO-CH_3)$ |
| 1.090 | H | $CH_3$ | $CH_3$ | H | $CH_2CH_2$ | $CH(COO-CH_3)$ |
| 1.091 | H | H | H | H | $CH_2CH_2$ | $C(CN)-(COOCH_3)$ |
| 1.092 | H | H | OH | $CH_3$ | $CH_2CH_2$ | $CH(COO-CH_3)$ |
| 1.093 | H | OH | H | H | $CH_2$ | $CH_2CH_2$ |
| 1.094 | H | $COOCH_3$ | H | H | $CH_2$ | $CH_2CH_2$ |
| 1.095 | H | COOH | H | H | $CH_2$ | $CH_2CH_2$ |
| 1.096 | H | H | H | H | $CH_2$ | $CH_2-CH(COO-CH_3)$ |
| 1.097 | H | $OCH_2CH_3$ | H | H | $CH_2$ | $CH_2CH_2$ |
| 1.098 | H | $OCH_2CH_3$ | H | H | $CH_2$ | $CH_2-CH(COO-CH_3)$ |

The process according to the invention is illustrated in more detail in the following Preparation Examples:

EXAMPLE P1

Preparation of 4-methylene-3-oxabicyclo[3.2.1] octan-2-one from 3-methylene-bicyclo[2.2.1]heptan-2-one (Comp.No. 1.001):

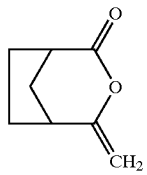

a) 98.7 g (0.81 mol) of 3-methylenebicyclo[2.2.1]heptan-2-one and 32.9 g (0.24 mol) of sodium acetate trihydrate in 400 ml of dichloromethane are used as the initial charge in a reaction vessel. While controlling the temperature ($CO_2$/acetone bath), 230 g of 32% peracetic acid in acetic acid (0.97 mol) are then added dropwise in the course of 2.5 hours, at a temperature of from −8° C. to −10° C. with stirring. The reaction mixture is subsequently stirred at a temperature of −8° C. for a further hour. 200 g of ice are then added, followed by 20 g (0.16 mol) of sodium sulfite in 100 ml of water. The organic phase is separated off and washed with water, dried over magnesium sulfate and concentrated to yield, in the form of a liquid residue, 81.9 g of 4-methylene-3-oxabicyclo[3.2.1]octan-2-one with a 93% content and a yield of 68.2%.

$^1$H-NMR (CDCl$_3$): 4.42 ppm, d, 1H; 4.18 ppm, d, 1H; 3.08 ppm, 2H; 1.95–2.08 ppm, 4H; 1.84 ppm, m, 1H; 1.67 ppm, m, 1H.

b) In a reaction vessel, 95.2 g of 3-methylenebicyclo[2.2.1] heptan-2-one are dissolved in 400 ml of methylene chloride; 32.6 g of sodium acetate trihydrate are added and the mixture is cooled to a temperature of −10° C. With stirring at a temperature of from −8 to −10° C., 199 ml of 36–40% peracetic acid are then fed in in the course of 2.40 hours and the reaction mixture is stirred for a further 2 hours at −10° C. The reaction mixture is subsequently added to 400 g of an ice/water mixture, and the organic phase is separated off and treated with a mixture of 100 g of ice and 100 ml of 15% sodium sulfite solution. The organic phase is then washed with 100 ml of 25% sodium carbonate solution and subsequently with 100 ml of water. The combined aqueous phases are washed with 200 ml of methylene chloride. The combined organic phases are subsequently concentrated at a bath temperature of 50° C. using a rotary evaporator. The remaining liquid is subjected to fractional distillation on a column at 53 Pa yielding, at a temperature of from 40 to 45° C., 27 g of 3-methylene-bicyclo[2.2.]heptan-2-one (starting material) and, at a temperature of from 55 to 60° C. 60 g of 4-methylene-3-oxabicyclo[3.2.1]octan-2-one, corresponding to a yield of 55.7% based on starting material used and to a selectivity of 77.8% (based on reacted starting material).

EXAMPLE P2

4-Methylene-3-oxabicyclo[3.2.2]nonan-2-one from 3-methylene-bicyclo[2.2.2]octan-2-one (Comp. No. 1.070):

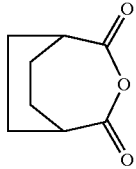

Analogously to the procedure indicated in Example P1, 955 mg (7 mmol) of 3-methylene-bicyclo[2.2.2]octan-2-one is reacted with 1.64 g (8.4 mmol) of 32% peracetic acid in the presence of 286 mg (21 mmol) of sodium acetate trihydrate. 1 g of 4-methylene-3-oxa-bicyclo[3.2.2]nonan-2-one is isolated. After purification by column chromatography using 10% ethyl acetate in hexane, pure 4-methylene-3-oxabicyclo[3.2.2]nonan-2-one is obtained in the form of an oil.

$^1$H-NMR (CDCl$_3$): 4.62 ppm, "s", 1H; 4.25 ppm, "s", 1H; 2.9–3.0 ppm, 2H; 1.9–2.1 ppm, 2H; 1.7–1.9 ppm, 6H.

EXAMPLE P3

Preparation of the Triethylammonium Salt of 4-hydroxybicyclo[3.2.1]oct-3-en-2-one from 4-methylene-3-oxabicyclo[3.2.1]octan-2-one:

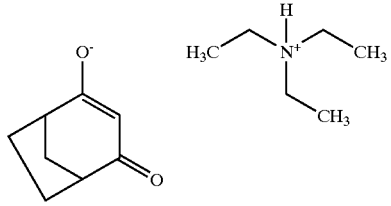

2.76 g (20 mmol) of 4-methylene-3-oxabicyclo[3.2.1]octan-2-one are heated to a temperature of 55° C. for 2.5 hours in the presence of 2.23 g (20 mmol) of triethylamine and 0.13 g (2 mmol) of potassium cyanide. The turbid reaction mixture is filtered over Hyflo® and evaporated to dryness. The triethylammonium salt of 4-hydroxybicyclo[3.2.1]oct-3-en-2-one is obtained in the form of a resinous, hygroscopic product.

EXAMPLE P4

Preparation of the Ethyldiisopropylammonium Salt of 4-hydroxy-bicyclo[3.2.1]oct-3-en-2-one from 4-methylene-3-oxabicyclo[3.2.1]octan-2-one:

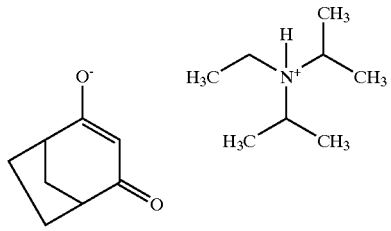

Analogously to Example P3, 1.38 g (10 mmol) of 4-methylene-3-oxabicyclo[3.2.1]octan-2-one is stirred for a period of 12 hours in the presence of 1.29 g (10 mmol) of Hünig's base and 0.13 g of potassium cyanide in 10 ml of acetonitrile. Solid components (potassium salts) are filtered off and the filtrate is evaporated to dryness to yield the ethyldiisopropyl-ammonium salt of 4-hydroxybicyclo[3.2.1]oct-3-en-2-one in the form of a resin.

EXAMPLE P5

Preparation of the Sodium Salt of 4-hydroxybicyclo[3.2.1]oct-3-en-2-one:

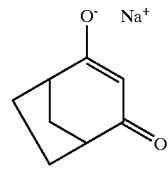

At a temperature of 110° C., a 30% solution of 12.1 g (0.22 mol) of sodium methanolate in methanol is added dropwise to a solution of 190 ml of toluene and 10 ml of dimethylformamide, the methanol being removed continuously by distillation. There are then added dropwise to the resulting suspension over a period of 30 minutes, with removal of methanol by distillation being continued, 20.7 g (0.15 mol) of 4-methylene-3-oxabicyclo[3.2.1]octan-2-one dissolved in 20 ml of toluene. After stirring for a further 2 hours at boiling temperature, the reaction mixture is allowed to cool and the precipitated product is filtered off and washed with toluene.

EXAMPLE P6

Conversion of the Sodium Salt from Example P5 to bicyclo[3.2.1 octane-2,4-dione

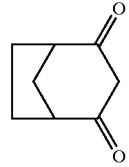

The sodium salt of 4-hydroxybicyclo[3.2.1]oct-3-en-2-one obtained above is introduced into 300 ml of ice-water and adjusted to pH 3 using concentrated hydrochloric acid, neutral bicyclo[3.2.1]octane-2,4-dione precipitating in the form of a solid, which is extracted with ethyl acetate, washed with water, dried over sodium sulfate and concentrated to approximately 50 ml by evaporation. The precipitated product, 15.2 g (73.3%), is pure bicyclo[3.2.1]octane-2,4-dione having a melting point of 128–129° C.

EXAMPLE P7

Direct Conversion to bicyclo[3.2.1]octane-2,4-dione Without Isolation of the Sodium Salt of 4-hydroxybicyclo[3.2.1]oct-3-en-2-one:

4.27 g (79 mmol) of sodium methanolate in 40 ml of dimethyl sulfoxide are used as initial charge in a reaction vessel. A solution of 7.2 g (52 mmol) of 4-methylene-3-oxabicyclo(3.2.1]octan-2-one in 20 ml of dimethyl sulfoxide is fed into that solution in the course of 2.5 hours at a temperature of from 25 to 35° C., with stirring. After a further 0.5 hours, the reaction mixture is diluted with 200 ml of water and extracted twice with 100 ml of ethyl acetate.

The combined organic phases are washed with 100 ml of water. The aqueous phases are then combined, adjusted to pH 3 using approximately 35 ml of 2N hydrochloric acid, and extracted four times using 400 ml of ethyl acetate each time. The combined organic phases are washed with water, dried over magnesium sulfate, filtered and concentrated using a rotary evaporator. The brown solid remaining is filtered over silica gel and yields 6.3 g (46 mmol) of bicyclo[3.2.1]octane-2,4-dione with a content of 93%, corresponding to a yield of 81.4%, and a melting point of 129–130° C.

EXAMPLE P8

Direct Conversion to bicyclo[3.2.1]octane-2,4-dione Without Isolation of the Triethylammonium Salt of 4-hydroxybicyclo[3.2.1]oct-3-en-2-one:

Analogously to Example P3, 2.76 g (20 mmol) of 4-methylene-3-oxabicyclo[3.2.1]octan-2-one are stirred for 15 hours at room temperature in the presence of 2.23 g (22 mmol) of triethylamine and 0.13 g (2 mmol) of potassium cyanide in 10 ml of acetonitrile. The mixture is heated at 55° for a further 30 minutes and then taken up in water and the neutral components are removed at pH 10 using ethyl acetate. The aqueous phase, acidified to pH 2, is extracted with ethyl acetate, dried over sodium sulfate and concentrated by evaporation, yielding 2.05 g (74.3%0) of pure bicyclo[3.2.1]octane-2,4-dione having a melting point of 129–130° C.

What is claimed is:

1. A process for the preparation of a compound of formula I

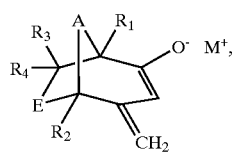

(I)

wherein $R_1$, $R_2$, $R_3$ and $R_4$ are each independently of the others hydrogen, $C_1$–$C_4$alkyl, halogen, hydroxy, $C_1$–$C_4$alkoxy, $C_1$–$C_4$alkoxycarbonyl, hydroxycarbonyl or cyano; A and E are each independently of the other $C_1$–$C_2$alkylene, which may be substituted once or up to four times by a $C_1$–$C_4$alkyl group or by halogen, hydroxy, $C_1$–$C_4$alkoxy, $C_1$–$C_4$alkoxy-carbonyl or cyano, and M+ is an alkali metal ion, alkaline earth metal ion or ammonium ion, which comprises a) reacting a compound of formula II

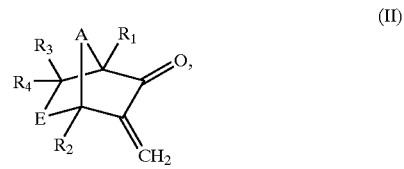

(II)

wherein $R_1$, $R_2$, $R_3$, $R_4$, A and E are as defined for formula I, in the presence of an oxidising agent, to form a compound of formula III

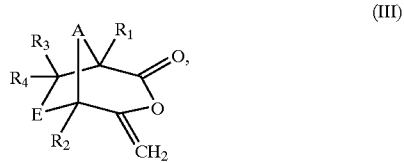

(III)

wherein $R_1$, $R_2$, $R_3$, $R_4$, A and E are as defined for formula I, and b) then converting that compound to a salt of formula I either in the presence of a base and a catalytic amount of a cyanide or in the presence of an alkali metal alcoholate or alkaline earth metal alcoholate or a hydroxide.

2. A compound of formula III

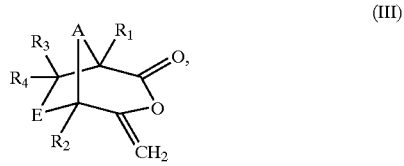

(III)

wherein $R_1$, $R_2$, $R_3$, $R_4$, A and E are as defined for formula I in claim 1.

* * * * *